(12) United States Patent
Breyne et al.

(10) Patent No.: US 6,558,583 B2
(45) Date of Patent: May 6, 2003

(54) NAPHTHOPYRANS ANNELATED IN $C_5$-$C_6$ WITH A DIHYDROBENZO-CYCLOHEPTATRIENE-TYPE CARBOCYCLE AND COMPOSITIONS AND MATRICES CONTAINING THEM

(75) Inventors: Olivier Breyne, Lyons (FR); You-Ping Chan, Lyons (FR); Jean Patrick, Lyons (FR)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/974,357

(22) Filed: Oct. 9, 2001

(65) Prior Publication Data

US 2002/0125463 A1 Sep. 12, 2002

(30) Foreign Application Priority Data

Oct. 11, 2000 (FR) .......................... 2000 12985

(51) Int. Cl.$^7$ .......................... G02B 5/23; C07D 311/78; C07C 39/12
(52) U.S. Cl. .................. 252/586; 549/382; 549/381; 549/331; 351/163; 568/732; 524/110
(58) Field of Search .................... 252/586; 351/163; 549/382, 381, 331; 568/732; 524/110

(56) References Cited

U.S. PATENT DOCUMENTS

| | | | | |
|---|---|---|---|---|
| 3,567,605 A | * | 3/1971 | Becker ..................... | 204/158 |
| 3,627,690 A | * | 12/1971 | Framingham et al. ...... | 252/300 |
| 4,826,977 A | * | 5/1989 | Heller et al. ................. | 544/70 |
| 5,200,116 A | * | 4/1993 | Heller ......................... | 252/586 |
| 5,238,981 A | * | 8/1993 | Knowles .................... | 524/110 |
| 5,411,679 A | * | 5/1995 | Kumar ....................... | 252/586 |
| 5,429,744 A | * | 7/1995 | Hagqvist ................. | 210/493.1 |
| 5,451,344 A | * | 9/1995 | Knowles et al. ............ | 252/586 |
| 5,498,814 A | * | 3/1996 | Chang et al. ............... | 252/586 |
| 5,527,911 A | * | 6/1996 | Guglielmetti et al. ....... | 544/250 |
| 5,631,720 A | * | 5/1997 | Guglielmetti et al. ....... | 351/163 |
| 5,645,767 A | * | 7/1997 | Van Gemert ............... | 252/586 |
| 5,651,923 A | * | 7/1997 | Kumar et al. .............. | 252/586 |
| 5,698,141 A | * | 12/1997 | Kumar ..................... | 252/586 |
| 5,754,271 A | * | 5/1998 | Guglielmetti et al. ....... | 351/163 |
| 5,783,116 A | * | 7/1998 | Lin ........................... | 252/586 |

FOREIGN PATENT DOCUMENTS

| | | | | |
|---|---|---|---|---|
| EP | 0 562 915 | * | 3/1993 | ......... C07D/491/04 |
| FR | 2 718 447 | * | 10/1995 | |
| WO | WO 94/22850 | * | 10/1994 | ......... C07D/311/92 |
| WO | WO 95/05382 | * | 2/1995 | ......... C07D/491/04 |
| WO | WO 96/14596 | * | 5/1996 | ............ G02B/5/23 |
| WO | WO 97/21698 | * | 6/1997 | ......... C07D/311/78 |
| WO | WO 98/50443 | * | 11/1998 | ......... C08F/226/02 |
| WO | WO 00/15628 | * | 3/2000 | ......... C07D/311/92 |

OTHER PUBLICATIONS

J.C. Crano et al., Spiroxazines and their use in photochromic lenses, Applied Photochromic Polymers Systems, Chapter 2, 1992.*
Edens et al., Mechanism of the Meyer–Schuster Rearrangement, J. Org. Chem., vol. 42, No. 21, 1977, pp. 3403–3408.*
dialogweb.com, abstract for FR 2718447 from Derwent WPI, pp. 1–3, Mar. 30, 2001.*

* cited by examiner

Primary Examiner—Philip Tucker
(74) Attorney, Agent, or Firm—Timothy M. Schaeberle; Siwen Chen

(57) ABSTRACT

The invention relates to novel naphthopyran-type compounds, which are annelated in position $C_5$–$C_6$ with a seven-membered carbocycle, and which are of formula (I) given below:

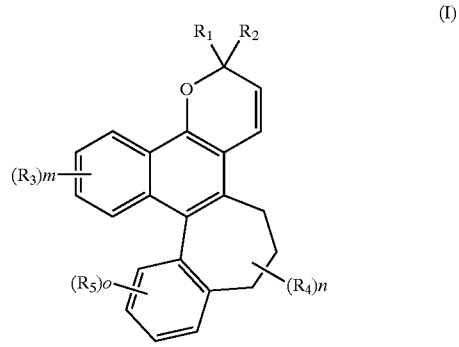

These compounds (I) possess interesting photochromic properties. The invention also relates to their preparation, their applications as photochromes as well as the compositions and (co)polymer matrices containing them.

20 Claims, No Drawings

NAPHTHOPYRANS ANNELATED IN $C_5$-$C_6$ WITH A DIHYDROBENZO-CYCLOHEPTATRIENE-TYPE CARBOCYCLE AND COMPOSITIONS AND MATRICES CONTAINING THEM

The present invention relates to novel naphthopyran-type compounds which are annelated in $C_5$–$C_6$ with a dihydrobenzocycloheptatriene-type carbocycle, and which have, in particular, photochromic properties. The invention also relates to photochromic compositions and photochromic ophthalmic articles (lenses for example) which contain said naphthopyrans. The invention also covers the preparation of these novel compounds.

The photochromic compounds are capable of changing color under the influence of a poly- or mono-chromatic light (UV for example) and of returning to their initial color when the luminous irradiation ceases, or under the influence of temperature and/or a poly- or mono-chromatic light different from the first.

The photochromic compounds find applications in various fields, e.g. for the manufacture of ophthalmic lenses, contact lenses, solar protection glasses, filters, camera optics or photographic apparatus optics or other optical devices and observation devices, glazing, decorative objects, bill elements or even for information storage by optical inscription (coding).

In the field of ophthalmic optics, and in particular the spectacles trade, a photochromic lens which comprises one or more photochromic compounds must have:

- a high transmission in the absence of ultraviolets,
- a low transmission (high colorability) under solar irradiation,
- adapted coloration and discoloration kinetics,
- a tint acceptable to the consumer (grey or brown preferably) with preferably a maintenance of the chosen tint during the coloration and the discoloration of the lens,
- a maintenance of the performances, the properties, within a temperature range of 0–40° C.,
- a significant durability, since these objectives sought after are sophisticated corrective lenses and therefore expensive.

These lens characteristics are in fact determined by the active photochromic compounds which they contain; compounds which must furthermore be perfectly compatible with the organic or inorganic, even hybrid support which constitutes the lens.

Moreover, it is to be noted that obtaining a grey or brown tint may necessitate the use of at least two photochromes of different colors, i.e. having distinct maximal absorption wavelengths in the visible. This combination further imposes other requirements of the photochromic compounds. In particular, the coloration and discoloration kinetics of the (two or more) combined active photochromic compounds must be essentially identical. The same applies for their stability with time and also for their compatibility with a plastic, inorganic or hybrid inorganic-organic support.

Amongst the numerous photochromic compounds described in the prior art, benzopyrans and naphthopyrans may be cited which are described in patents or patent applications: U.S. Pat. Nos. 3,567,605, 3,627,690, 4,826,977, 5,200,116, 5,238,981, 5,411,679, 5,429,744, 5,451,344, 5,458,814, 5,651,923, 5,645,767, 5,698,141, 5,783,116, WO-A-95 05382, FR-A-2,718,447, WO-A-96 14596, WO-A-97 21698, which are of the reduced formulae below:

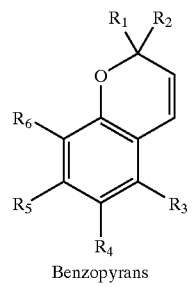
Benzopyrans

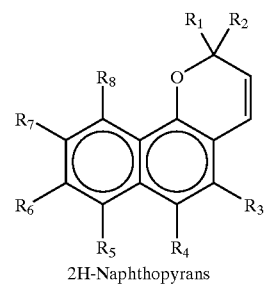
2H-Naphthopyrans

U.S. Pat. No. 5,645,767 describes naphthopyrans which have an indeno group linked to carbons 5 and 6 of the naphtho skeleton:

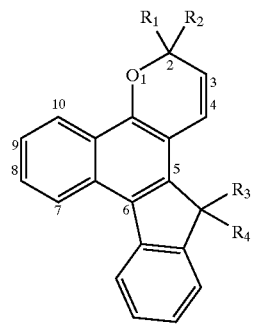

U.S. Pat. No. 5,783,116 describes naphthopyrans which have a non-substituted alicyclic group

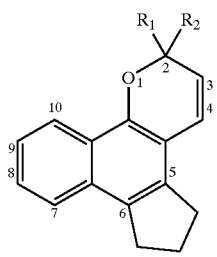 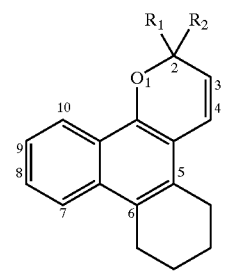

Patent application WO 00/15628 of the Applicant describes naphthopyrans which have an alicyclic group which is substituted or fused with an aromatic:

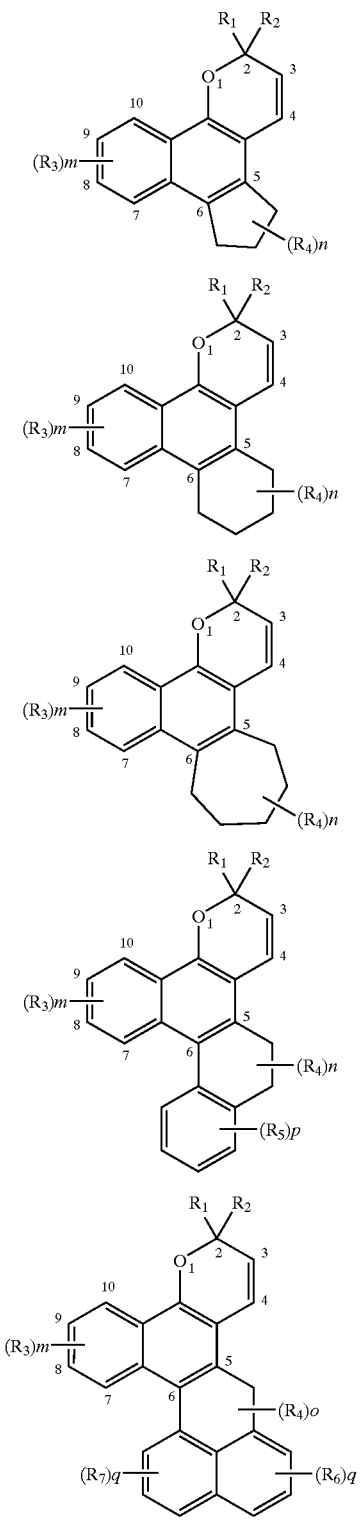

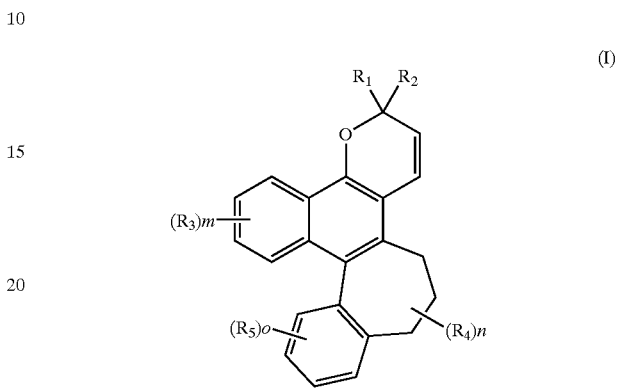

These compounds claim to satisfy the specifications defined above. In reality, if these compounds really do have one or more of the basic properties sought after, such as a high transmission in the absence of ultraviolets and a high colorability under solar irradiation, none of the compounds described hitherto have the complete combination of the properties sought after which are necessary for the production of satisfactory articles.

In this context, it is to the credit of the inventors for having been interested in this type of derivative as a basis for the development of novel photochromes and for having proposed a novel family of molecules having particularly advantageous photochromic properties.

Thus, according to a first of its aspects, the present invention relates to compounds of the following formula (I):

in which:
$R_1$ and $R_2$, which are identical or different, independently represent:
hydrogen,
a linear or branched alkyl group comprising 1 to 12 carbon atoms,
a cycloalkyl group comprising 3 to 12 carbon atoms,
an aryl or heteroaryl group comprising in its basic structure 6 to 24 carbon atoms or 4 to 24 carbon atoms respectively and at least one heteroatom selected from sulphur, oxygen and nitrogen; said basic structure being optionally substituted with at least one substituent selected from the whole of the substituents given below:
a halogen, and notably fluorine, chlorine and bromine,
a hydroxy,
a linear or branched alkyl group comprising 1 to 12 carbon atoms,
a linear or branched alkoxy group comprising 1 to 12 carbon atoms, or a silyloxy group,
a haloalkyl or haloalkoxy group corresponding to the ($C_1$–$C_{12}$) alkyl or alkoxy groups above respectively which are substituted with at least one halogen atom, and notably a fluoroalkyl group of this type,
a phenoxy or naphthoxy group optionally substituted with at least one linear or branched alkyl or alkoxy group comprising 1 to 12 carbon atoms,
a linear or branched alkenyl or alkynyl group comprising 2 to 12 carbon atoms, and notably a vinyl group or an allyl group,
an —$NH_2$ group,
an —NHR group, R representing a linear or branched alkyl group comprising 1 to 6 carbon atoms, or a phenyl group optionally substituted with at least one linear or branched alkyl group comprising 1 to 6 carbon atoms, a

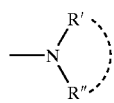

group, R' and R", which are identical or different, representing independently a linear or branched alkyl group comprising 1 to 6 carbon atoms, or a phenyl group optionally substituted with at least one linear or branched alkyl group comprising 1 to 6 carbon atoms, or representing together with the nitrogen atom to which they are bound a 5- to 7-membered ring which can comprise at least one other heteroatom selected from oxygen, sulphur and nitrogen, said nitrogen being optionally substituted with an R∴' group, which is a linear or branched alkyl group comprising 1 to 6 carbon atoms, a methacryloyl group or an acryloyl group;
and/or said basic structure being optionally annelated with an aromatic or non-aromatic cyclic group, which can comprise at least one heteroatom selected from the group comprising: oxygen, sulphur or nitrogen, which comprises one or two annelated rings; the ring(s), which is (are) independently aromatic or non-aromatic, and which is (are) 5- to 7-membered, being optionally substituted with at least one substituent selected from those listed above;

an aralkyl or heteroaralkyl group, the alkyl group of which, which is linear or branched, comprises 1 to 4 carbon atoms and the aryl part or heteroaryl part of which has the same definition as that given above for the aryl or heteroaryl group; or said two substituents $R_1$ and $R_2$ together form an adamantyl, norbornyl, fluorenylidene, di($C_1$–$C_6$) alkylanthracenylidene, or spiro($C_5$–$C_6$) cycloalkylanthracenylidene group; said group being optionally substituted with at least one of the substituents listed above for $R_1$, $R_2$ where $R_1$ and $R_2$ represent an aryl or heteroaryl group;

$R_3$, which are identical or different, independently represent:
a hydroxy,
a halogen, and notably fluorine, chlorine or bromine,
a linear or branched alkyl group comprising 1 to 12 carbon atoms (advantageously 1 to 6 carbon atoms),
a cycloalkyl group comprising 3 to 12 carbon atoms,
a linear or branched alkoxy group comprising 1 to 12 carbon atoms (advantageously 1 to 6 carbon atoms), or a silyloxy group,
a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
a linear or branched alkenyl or alkynyl group comprising 2 to 12 carbon atoms, and notably a vinyl group or an allyl group, an aryl or heteroaryl group having the same definition as that given above for $R_1$, $R_2$,
an aralkyl or heteroaralkyl group, the alkyl group, which is linear or branched, comprises 1 to 4 carbon atoms, and the aryl and heteroaryl groups having the same definitions as those given above for $R_1$, $R_2$,
a phenoxy or naphthoxy group optionally substituted with at least one linear or branched alkyl or alkoxy group comprising 1 to 12 carbon atoms,
an amine or amide group: —$NH_2$, —NHR, —$CONH_2$, —CONHR,

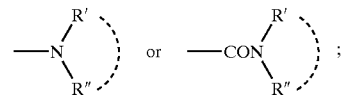

R, R', R" having their respective definitions given above for the amine substituents of the values $R_1$, $R_2$:
aryl or heteroaryl,
an —$OCOR_6$ or —$COOR_6$ group, wherein $R_6$ represents a linear or branched alkyl group comprising 1 to 6 carbon atoms, or a cycloalkyl group comprising 3 to 6 carbon atoms, or a phenyl group, optionally substituted with at least one of the substituents listed above for $R_1$, $R_2$ where $R_1$ and $R_2$ represent an aryl or heteroaryl group; or
at least two of the adjacent $R_3$ groups together form an aromatic or non-aromatic cyclic group, which aromatic or non-aromatic cyclic group optionally comprises at least one heteroatom selected from oxygen, sulphur and nitrogen and which aromatic or non-aromatic cyclic group optionally comprises one or two 5- to 7-membered annelated rings, which is (are) independently aromatic or non-aromatic and which is (are) optionally substituted with at least one of the substituents listed above for $R_1$, $R_2$ where $R_1$ and $R_2$ represent an aryl or heteroaryl group;

m is an integer of 0 to 4;

$R_4$, which are identical or different, independently represent a hydroxy, a linear or branched alkyl or alkoxy group comprising 1 to 6 carbon atoms, or two of the $R_4$ groups together form a carbonyl (C=O);

n is an integer of 0 to 6;

$R_5$, which are identical or different, independently represent:
a halogen, and notably fluorine, chlorine or bromine,
a hydroxy,
a linear or branched alkyl group comprising 1 to 12 carbon atoms (advantageously 1 to 6 carbon atoms),
a cycloalkyl group comprising 3 to 12 carbon atoms,
a linear or branched alkoxy group comprising 1 to 12 carbon atoms (advantageously 1 to 6 carbon atoms),
a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
a phenyl or benzyl group which is optionally substituted with at least one of the substituents listed above in the definition of the $R_1$, $R_2$ radicals of formula (1) in the case in which the radicals independently correspond to an aryl or heteroaryl, a phenoxy group optionally substituted with at least one linear or branched alkyl or alkoxy group comprising 1 to 12 carbon atoms,
an amine or amide group: —NH₂, —NHR, —CONH₂, —CONHR,

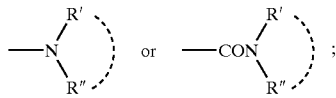

R, R' and R" having their respective definitions given above for the amine substituents of the values $R_1$, $R_2$ where $R_1$ and $R_2$ represent an aryl or heteroaryl group, or an —OCOR₇ or —COOR₇ group, wherein $R_7$ represents a linear or branched alkyl group comprising 1 to 6 carbon atoms, or a cycloalkyl group comprising 3 to 6 carbon atoms, or a phenyl or benzyl group, optionally substituted with at least one of the substituents listed above for $R_1$, $R_2$ where $R_1$ and $R_2$ represent an aryl or heteroaryl group; or at least two of the adjacent $R_5$ groups together form an aromatic or non-aromatic cyclic group, which aromatic or non-aromatic cyclic group optionally comprises at least one heteroatom selected from oxygen, sulphur and nitrogen and which aromatic or non-aromatic cyclic group optionally comprises one or two 5- to 7-membered annelated rings, which is (are) independently aromatic or non-aromatic and which is (are) optionally substituted with at least one of the substituents listed above for the values of $R_1$, $R_2$ where $R_1$ and $R_2$ represent an aryl or heteroaryl group; and o is an integer of 0 to 4.

The person skilled in the art will obviously have understood that the branched alkyl, alkoxy and alkenyl groups as defined above comprise a number of carbons which is sufficient to be able to be branched (more than 3, more than 3 and more than 4 carbon atoms, respectively).

The compounds of the invention—annelated naphthopyrans of formula (I)—possess rapid discoloration kinetics combined with a strong colorability.

Amongst said compounds of the invention, preferred are those which are of formula (I) in which:

$R_1$, $R_2$ are identical or different and represent independently optionally substituted aryl or heteroaryl groups the basic structure of which is selected from the group comprising phenyl, naphthyl, biphenyl, pyridyl, furyl, benzofuryl, dibenzofuryl, N—(C₁–C₆)alkylcarbazole, thienyl, benzothienyl, dibenzothienyl and julolidinyl groups; $R_1$ and/or $R_2$ representing, advantageously, a para-substituted phenyl group; or $R_1$ and $R_2$ together form an adamantyl or norbornyl group;

$R_3$ and $R_5$ independently represent a halogen, an alkyl group or an alkoxy group; and m and o=1 and n=0.

According to a second of its aspects, the present invention relates to a method of preparing compounds (I), characterised in that it comprises a condensation:

of an intermediate product of formula (II) given below:

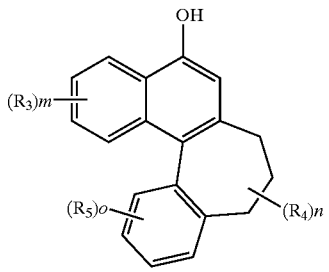

in which $R_3$, $R_4$, $R_5$, m, n and o are as defined above with reference to formula (I);

with a derivative of propargylic alcohol, having formula (III) below:

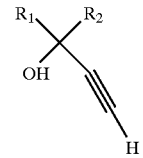

in which $R_1$ and $R_2$ are as defined above with reference to formula (I);

the condensation (II)/(III) being carried out advantageously in the presence of a catalyst, this catalyst being preferably selected from the group comprising para-toluenesulphonic acid, dodecylsulphonic acid or bromoacetic acid; or with an aldehyde derivative, having formula (III') below:

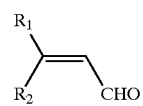

in which $R_1$ and $R_2$ are as defined above with reference to formula (I);

the condensation (II)/(III') being carried out, advantageously, in the presence of a metallic complex, preferably a complex of titanium, titanium (IV) ethoxide being particularly preferred.

In practice, the condensation reaction between compounds (II) and (III) or (III') can take place in solvents such as toluene, xylene or tetrahydrofuran, to which appropriate catalysts are optionally added. For more details on the condensation of compounds (II) and (III'), reference may be made to the EP-A-0 562 915 patent application.

The compounds of formula (III) are known to the person skilled in the art and are obtained from the corresponding ketone according to a method described notably in the WO-A-96 14596 patent application. The ketone is itself commercial or is prepared according to the known methods such as the Friedel Crafts method (cf. WO-A-96 14596 and cited references).

Aldehydes (III'), which are derivatives of (III), are obtained by rearrangement in an acid medium (cf *J. Org. Chem.*, 1977, 42, 3403).

The compounds of formula (II) are obtained according to a synthesis scheme which is adapted from that mentioned in the application WO 00/15628.

reticulates thus obtained can constitute photochromic matrices such as those presented infra.

According to a fifth of its aspects, the present invention relates to the use of said compounds of formula (I) of the invention as photochromic agents. Another object of the invention is, therefore:

firstly, novel photochromic compounds which are constituted by the naphthopyran derivatives which are annelated in $C_5$–$C_6$ such as defined above, taken alone or in a mixture of themselves and/or with at least one other photochromic compound of another type and/or with at least one non-photochromic coloring agent;

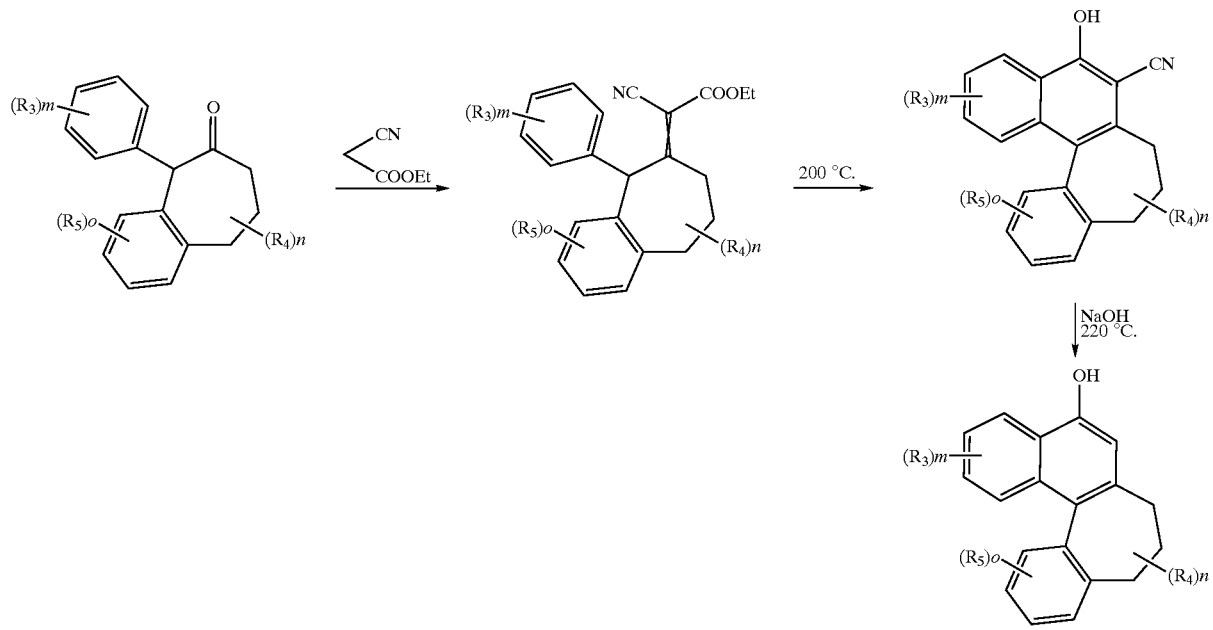

According to a third of its aspects, the invention also relates to novel intermediate products of formula (II) given below:

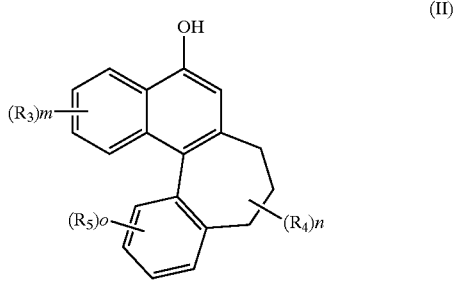

in which $R_3$, $R_4$, $R_5$, m, n and o are as defined above with reference to formula (I).

According to a fourth of its aspects, the object of the invention is (co)polymer(s) and/or reticulate(s) obtained by polymerising and/or cross-linking and/or grafting at least one compound (I) as defined above. The compounds (I) according to the invention can be per se (co)monomers and/or be comprised in (co)polymerisable and/or cross-linkable (co)monomers mixtures. The (co)polymers and/or secondly, novel photochromic compositions which comprise at least one compound (I) as defined above, and/or at least one linear or cross-linked (co)polymer containing at least one compound (I) according to the invention in its structure. Such photochromic compositions can contain at least one other photochromic compound, of another type and/or at least one non-photochromic coloring agent and/or at least one stabilising agent. These photochromic compounds of another type, non-photochromic coloring agents, and stabilising agents are prior art products known to the person skilled in the art.

Within the context of the present invention, combinations of photochromic compounds of the invention and/or combinations of photochromic compounds of the invention and photochromic compounds of another type according to the prior art are particularly recommended; such combinations being interesting in that they are suitable for generating grey or brown tints, which are desired by the public in applications such as ophthalmic spectacles or solar spectacles. These additional photochromic compounds can be those known to the person skilled in the art and described in the literature, e.g. chromenes (U.S. Pat. Nos. 3,567,605, 5,238,981, WO-A-94 22850, EP-A-0 562 915), spiropyrans or naphthospiropyrans (U.S. Pat. No. 5,238,981) and spiroxazines (Crano et al., "Applied Photochromic Polymer Systems ", Ed. Blackie & Son Ltd, 1992, chapter 2).

Said compositions according to the invention can also comprise:

non-photochromic coloring agents which enable adjusting the tint, and/or one or more stabilising agents, such as an antioxidising agent for example, and/or one or more anti-UV, and/or one or more anti-radicals, and/or one or more photochimic excited state deactivators.

These additives can notably enable improving the durability of said compositions.

The compounds of the invention envisaged within the context of their photochromic applications can be used in solution. Thus, a photochromic solution can be obtained by dissolving at least one of said compounds in an organic solvent such as toluene, dichloromethane, tetrahydrofuran or ethanol. The solutions obtained are in general colorless and transparent. When exposed to sunlight, they develop a strong coloration and regain the colorless state when they are placed in an area of less exposure to the sun's rays or, in other words, when they are no longer subjected to UV. In general, a very low concentration of product (of the order of 0.01 to 5% by weight) is sufficient to obtain an intense coloration.

The compounds according to the invention are furthermore compatible with support matrices of organic polymer or of inorganic material (even in a hybrid inorganic-organic material), in a form included in said matrices as well as in the form of a coating of said matrices.

Also, within the context of the fifth aspect of the invention in relation to the photochromic applications, the object of the invention is a matrix which comprises:

the (co)polymer, from a suspension or solution of the photochrome, in a silicone oil, in an aliphatic or aromatic hydrocarbon, or in a glycol, or from another polymer matrix, can be cited for example. The diffusion is commonly carried out at a temperature of 50 to 200° C. for a period of time of 15 minutes to several hours, according to the nature of the polymer matrix. Another implementation technique consists in mixing the photochrome in a formulation of polymerisable materials, depositing this mixture on a surface or in a mould, and then carrying out the copolymerisation. These implementation techniques, and others, are described in the article by Crano et al. "Spiroxazines and their use in photochromic lenses" published in Applied Photochromic Polymer Systems, Ed. Blackie and Son Ltd—1992.

The following products may be mentioned as examples of preferred polymer materials for forming matrices which are useful in optical applications of the photochromic compounds according to the invention:

those obtained from alkyl, cycloalkyl, (poly or oligo) ethylene glycol, aryl or arylalkyl mono-, di- tri- or tetraacrylate or mono-, di-, tri- or tetramethacrylate, which is optionally halogenated or which comprises at least one ether and/or ester and/or carbonate and/or carbamate and/or thiocarbamate and/or urea and/or amide group, polystyrene, polyether, polyester, polycarbonate (e.g. bisphenol-A polycarbonate, diallyl diethylene glycol polycarbonate), polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral, those obtained from difunctional monomers having the formula below:

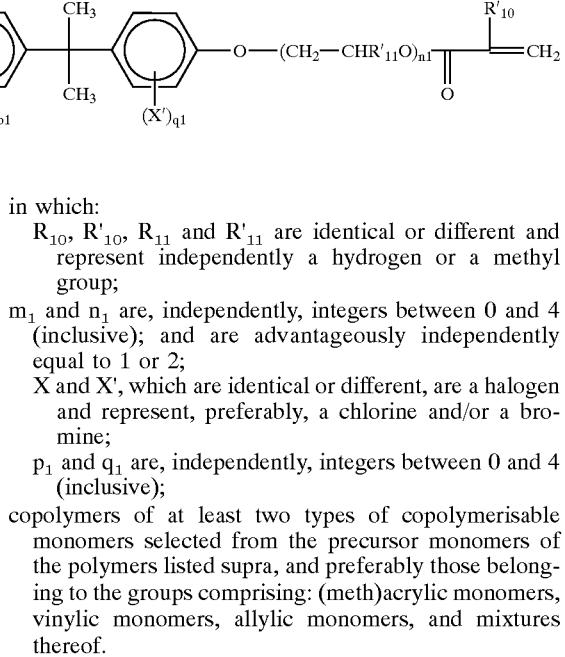

at least one compound of formula (1), as defined supra;

and/or at least one (co)polymer and/or reticulate, as defined supra;

and/or at least one composition, as presented above.

The most interesting applications of the compounds of the invention are in fact those in which the photochrome is dispersed uniformly within or on the surface of a matrix formed by a polymer and/or copolymer and/or mixture of (co)polymers.

Following the example of their behaviour in solution, the compounds (I), included in a polymer matrix are colorless or slightly colored in the initial state and rapidly develop an intense coloration under a UV light (365 nm) or under a light source of the solar type. Finally, they regain their initial coloration once the irradiation ceases.

The methods of implementation which can be envisaged in order to obtain such a matrix are very varied. Amongst those known to the person skilled in the art, the diffusion in in which:

$R_{10}$, $R'_{10}$, $R_{11}$ and $R'_{11}$ are identical or different and represent independently a hydrogen or a methyl group;

$m_1$ and $n_1$ are, independently, integers between 0 and 4 (inclusive); and are advantageously independently equal to 1 or 2;

X and X', which are identical or different, are a halogen and represent, preferably, a chlorine and/or a bromine;

$p_1$ and $q_1$ are, independently, integers between 0 and 4 (inclusive);

copolymers of at least two types of copolymerisable monomers selected from the precursor monomers of the polymers listed supra, and preferably those belonging to the groups comprising: (meth)acrylic monomers, vinylic monomers, allylic monomers, and mixtures thereof.

In a particularly preferred manner, the photochromes of the invention are used with resins which have a nanobiphasic structure and which are obtained by copolymerising at least two different, specific difunctional monomers. Such resins have been described by the Applicant in the patent application EP-A-0 977 788.

The amount of photochrome used in the (co)polymer matrix depends upon the degree of darkening desired. Usually, between 0.001 and 20% by weight of it is used.

Still according to the fifth of its aspects in relation to the applications of the compounds (I) as photochromes, another object of the present invention is ophthalmic articles, such as ophthalmic or solar spectacle articles, comprising:

- at least one compound of formula (1) according to the invention,
- and/or at least one (co)polymer and/or reticulate formed, at least in part, from compound(s) of the invention,
- and/or at least one photochromic composition as defined above,
- and/or at least one matrix (as defined supra), of an organic polymer material or of an inorganic material, or even of a hybrid inorganic-organic material, said matrix initially optionally comprising at least one compound of the invention.

In practice, the articles which are more particularly covered by the present invention are ophthalmic lenses or photochromic solar lenses, glazing (windows for buildings, for locomotion engines, automobile vehicles), optical devices, decorative articles, solar protection articles, information storage, . . . .

The present invention is illustrated by the Examples which follow, of synthesis and of photochromic validation, of a compound of the invention. Said compound of the invention is compared to a prior art compound C2.

EXAMPLES

Example 1

Synthesis of Compound (C1)

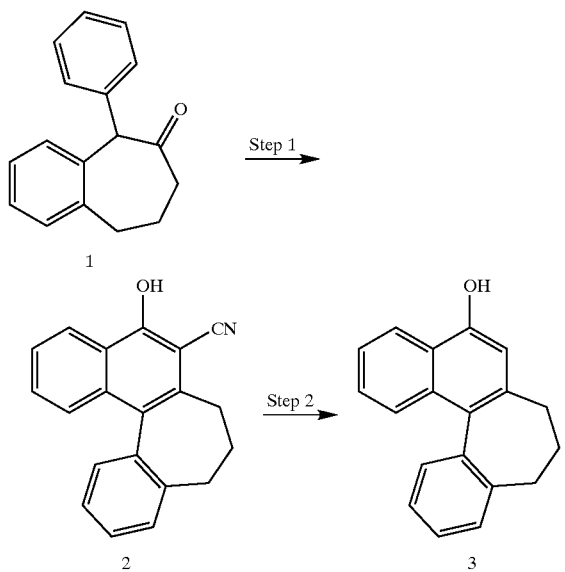

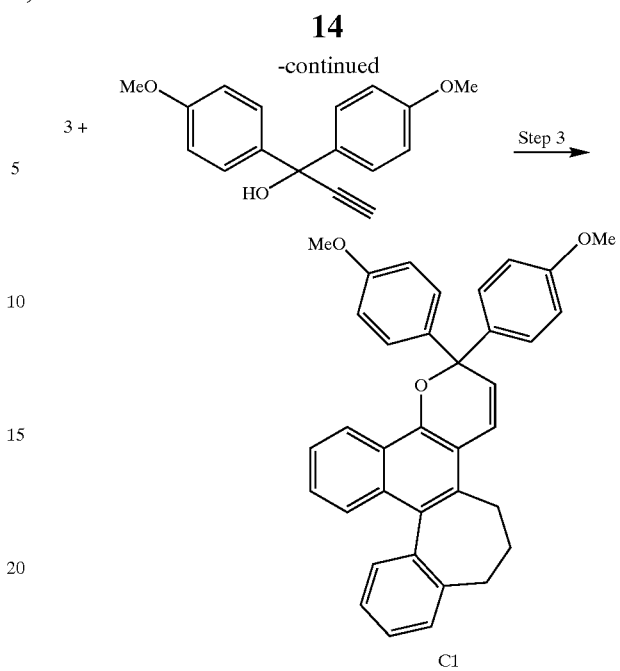

Remark: Ketone 1 is obtained from commercial benzosuberone according to a scheme adapted from that mentioned in the application WO 00/15628 of the Applicant.

Step 1:

A mixture of ketone 1 (2.18 g), ethyl cyanoacetate (1.05 g) and ammonium acetate (0.7 g) in 30 ml of toluene and 1.67 g of acetic acid are stirred under reflux for 4 hours 30 minutes. 4 g of acetamide are added, and the toluene is distilled off with a Dean Stark apparatus. Stirring is effected for 2 hours at 200° C., and the mixture is then poured, hot, into 20 ml of toluene. The solid obtained is filtered off. 40 ml of water are added and the mixture is extracted with dichloromethane. After evaporation of the solvent and purification by chromatography on silica, 350 mg of 2 are obtained which are used directly in the next step.

Step 2:

The product of step 1, 0.4 g of KOH and 12 ml of water are introduced into a digestion bomb. Heat is given at 230° C. (pressure) for 8 hours. The cooled reaction mixture is acidified with 6N HCl and the brown solid formed is filtered off and dried. 190 mg of naphthol 3 are obtained, the $^1$H NMR spectrum of which is in agreement.

Step 3:

10 mg of dodecylbenzenesulphonic acid are added to a solution of 190 mg of naphthol 3 and 250 mg of 1, 1-bis(p-methoxyphenyl)-propyn-1-ol in 10 ml of toluene. Stirring under reflux is effected for 1 hour 30 minutes, and the reaction mixture is then purified by filtering over silica. The solid obtained is recrystallised to give 100 mg of slightly pink crystals which are pure by $^1$H NMR.

Example 2

Compound (C2) of the Prior Art (Application WO 00/15628)

The photochromic properties of said compounds (C1) and (C2) were evaluated.

Said compounds were dissolved, at the rate of 5 mg in 50 ml of THF, and the UV-visible absorptions (optical path of 1 cm) is then measured before and after exposure to a UV source at 365 nm. The observation of the tints and the intensities developed is done by placing the solutions in the sun or before a solar simulator. The properties of these compounds are given in the Table below.

| COMPOUND | STRUCTURE | λ VIS* | T₁/₂** |
|---|---|---|---|
| (C1) | 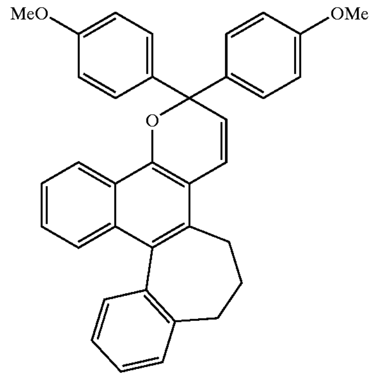 | 517 nm | 12 s |
| (C2) | 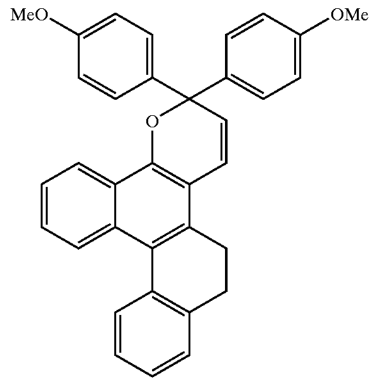 | 536 nm | 16 s |

\* λ VIS of the band of the highest intensity in the field of the visible spectrum of the compound after exposure.
\*\* discoloration time corresponding to 50% decrease of absorption at the λvis at ambient temperature.

The observation of the solutions of these compounds in the presence of sun's rays or UV rays shows that the compound of the invention has discoloration kinetics which is faster than the one of the compound of the prior art.

What is claimed:

1. A compound having the following formula (I):

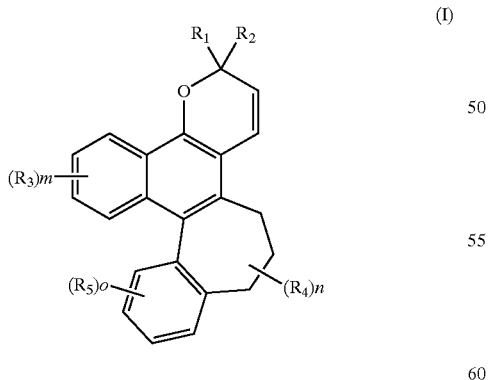

in which:
R₁ and R₂, which are identical or different, independently represent:
  hydrogen,
  a linear or branched alkyl group comprising 1 to 12 carbon atoms,
  a cycloalkyl group comprising 3 to 12 carbon atoms,
  an aryl group comprising, in its basic structure, 6 to 24 carbon atoms or a heteroaryl group comprising, in its basic structure, 4 to 24 carbon atoms and at least one heteroatom selected from sulphur, oxygen, and nitrogen; said basic structure being optionally substituted with at least one substituent selected from the group consisting of:
    a halogen,
    a hydroxy,
    a linear or branched alkyl group comprising 1 to 12 carbon atoms,
    a linear or branched alkoxy group comprising 1 to 12 carbon atoms,
    a silyloxy group,
    a haloalkyl or haloalkoxy group corresponding to the ($C_1$–$C_{12}$) alkyl or alkoxy groups above, respectively, which are substituted with at least one halogen atom,
    a phenoxy or naphthoxy group optionally substituted with at least one linear or branched alkyl or alkoxy group comprising 1 to 12 carbon atoms,
    a linear or branched alkenyl or alkynyl group comprising 2 to 12 carbon atoms,
    an —NH₂ group,
    an —NHR group, wherein R represents a linear or branched alkyl group comprising 1 to 6 carbon atoms or a phenyl group optionally substituted with at least one linear or branched alkyl group comprising 1 to 6 carbon atoms, a

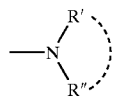

group, wherein R' and R", which are identical or different, independently represent a linear or branched alkyl group comprising 1 to 6 carbon atoms or a phenyl group optionally substituted with at least one linear or branched alkyl group comprising 1 to 6 carbon atoms, or wherein R' and R", together with the nitrogen atom to which they are bound, represent a 5- to 7-membered ring which optionally comprises at least one other heteroatom selected from oxygen, sulphur, and nitrogen, said nitrogen being optionally substituted with an R''' group, which is a linear or branched alkyl group comprising 1 to 6 carbon atoms, and a methacryloyl group or an acryloyl group;

and/or said basic structure being optionally annelated with an aromatic or non-aromatic cyclic group, which aromatic or non-aromatic cyclic group optionally comprises at least one heteroatom selected from oxygen, sulphur, and nitrogen and which aromatic or non-aromatic cyclic group optionally comprises one or two 5- to 7-membered annelated rings, which is (are) independently aromatic or non-aromatic and which is (are) optionally substituted with at least one substituent selected from those listed above; or an aralkyl or heteroaralkyl group, the alkyl part of which is linear or branched and comprises 1 to 4 carbon atoms and the aryl part or heteroaryl part of which has the same definition as that given above for the aryl and heteroaryl group; or said two substituents $R_1$ and $R_2$ together form an adamantyl, norbomyl, fluorenylidene, di($C_1$–$C_6$) alkylantbracenylidene, or spiro($C_5$–$C_6$) cycloalkylanthracenylidene group; said group being optionally substituted with at least one of the substituents listed above for $R_1$, $R_2$ where $R_1$ and $R_2$ represent an aryl or heteroaryl group;

$R_3$, which are identical or different, independently represent:
a hydroxy,
a halogen,
a linear or branched alkyl group comprising 1 to 12 carbon atoms,
a cycloalkyl group comprising 3 to 12 carbon atoms,
a linear or branched alkoxy group comprising 1 to 12 carbon atoms,
a silyloxy group,
a haloalkyl, halocycloalkyl, or haloalkoxy group corresponding to the alkyl, cycloalkyl, or alkoxy groups above, respectively, which are substituted with at least one halogen atom,
a linear or branched alkenyl or alkynyl group comprising 2 to 12 carbon atoms,
an aryl or heteroaryl group having the same definition as that given above for $R_1$, $R_2$,
an aralkyl or heteroaralkyl group, the alkyl part of which is linear or branched and comprises 1 to 4 carbon atoms and the aryl part or heteroaryl part of which has the same definition as that given above for $R_1$, $R_2$, a phenoxy or naphthoxy group optionally substituted with at least one linear or branched alkyl or alkoxy group comprising 1 to 12 carbon atoms, an amine or amide group: —$NH_2$, —NHR, —$CONH_2$, —CONHR,

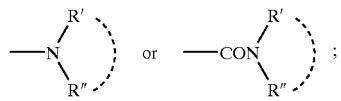

wherein R, R', and R" have their respective definitions given above, or an —$OCOR_6$ or —$COOR_6$ group, wherein $R_6$ represents a linear or branched alkyl group comprising 1 to 6 carbon atoms, or a cycloalkyl group comprising 3 to 6 carbon atoms, or a phenyl group, optionally substituted with at least one of the substituents listed above for $R_1$, $R_2$ where $R_1$ and $R_2$ represent an aryl or heteroaryl group; or at least two of the adjacent $R_3$ groups together form an aromatic or non-aromatic cyclic group, which aromatic or non-aromatic cyclic group optionally comprises at least one heteroatom selected from oxygen, sulphur, and nitrogen and which aromatic or non-aromatic cyclic group optionally comprises one or two 5- to 7-membered annelated rings, which is (are) independently aromatic or non-aromatic and which is (are) optionally substituted with at least one substituent selected from those listed above for $R_1$, $R_2$ where $R_1$ and $R_2$ represent an aryl or heteroaryl group;

m is an integer of 0 to 4;

$R_4$, which are identical or different, independently represent a hydroxy, a linear or branched alkyl or alkoxy group comprising 1 to 6 carbon atoms, or two of the $R_4$ groups together form a carbonyl (C=O);

n is an integer of 0 to 6;

$R_5$, which are identical or different, independently represent:
a halogen,
a hydroxy,
a linear or branched alkyl group comprising 1 to 12 carbon atoms,
a cycloalkyl group comprising 3 to 12 carbon atoms,
a linear or branched alkoxy group comprising 1 to 12 carbon atoms,
a haloalkyl, halocycloalkyl, or haloalkoxy group corresponding to the alkyl, cycloalkyl, or alkoxy groups above, respectively, which are substituted with at least one halogen atom,
a phenyl or benzyl group which is optionally substituted with at least one of the substituents listed above in the definition of the $R_1$, $R_2$ radicals of formula (I) in the case in which the radicals independently correspond to an aryl or heteroaryl,
a phenoxy group optionally substituted with at least one linear or branched alkyl or alkoxy group comprising 1 to 12 carbon atoms, an amine or amide group: —NH₂, —NHR, —CONH₂, —CONHR,

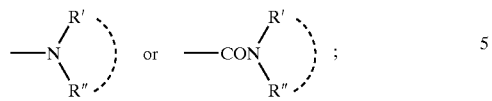

wherein R, R', and R" have their respective definitions given above for the amine substituents of $R_1$, $R_2$ where $R_1$ and $R_2$ represent an aryl or heteroaryl group, or an —OCOR₇ or —COOR₇ group, wherein R₇ represents a linear or branched alkyl group comprising 1 to 6 carbon atoms, or a cycloalkyl group comprising 3 to 6 carbon atoms, or a phenyl or benzyl group, optionally substituted with at least one of the substituents listed above for $R_1$, $R_2$ where $R_1$ and $R_2$ represent an aryl or heteroaryl group; or at least two of the adjacent $R_5$ groups together form an aromatic or non-aromatic cyclic group, which aromatic or non-aromatic cyclic group optionally comprises at least one heteroatom selected from oxygen, sulphur, and nitrogen and which aromatic or non-aromatic cyclic group optionally comprises one or two 5- to 7-membered annelated rings, which is (are) independently aromatic or non-aromatic and which is (are) optionally substituted with at least one substituent selected from those listed above for $R_1$, $R_2$ where $R_1$ and $R_2$ represent an aryl or heteroaryl group; and o is an integer of 0 to 4.

2. A compound according to claim 1, wherein:

$R_1$, $R_2$ are identical or different and independently represent optionally substituted aryl or heteroaryl groups, the basic structure of which is selected from the group consisting of phenyl, naphthyl, biphenyl, pyridyl, furyl, benzofuryl, dibenzofuryl, N—(C₁–C₆)alkylcarbazole, thienyl, benzothienyl, dibenzothienyl and julolidinyl groups; or $R_1$ and $R_2$ together form an adamantyl or norbornyl group;

$R_3$ and $R_5$ independently represent a halogen, an alkyl group, or an alkoxy group; and each of m and o is 1, and n is 0.

3. A compound according to claim 2, wherein each of $R_1$ and $R_2$ represents a para-substituted phenyl group.

4. A method of preparing a compound according to claim 1, said method comprising:

condensing an intermediate compound of the following formula (II):

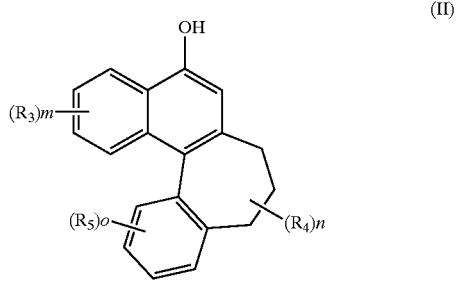

in which $R_3$, $R_4$, $R_5$, m, n, and o are as defined in claim 1 with a propargylic alcohol derivative having the following formula (III):

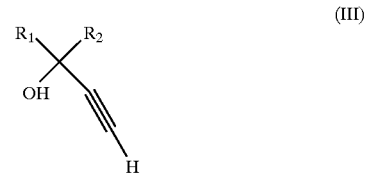

in which $R_1$ and $R_2$ are as defined in claim 1, wherein said condensing of (II)/(III) is optionally carried out in the presence of a catalyst, or with an aldehyde derivative having the following formula (III'):

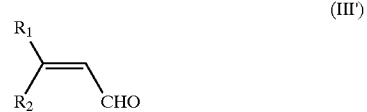

in which $R_1$ and $R_2$ are as defined in claim 1, wherein said condensing (II)/(III') is optionally carried out in the presence of a metallic complex.

5. A compound having the following formula (II):

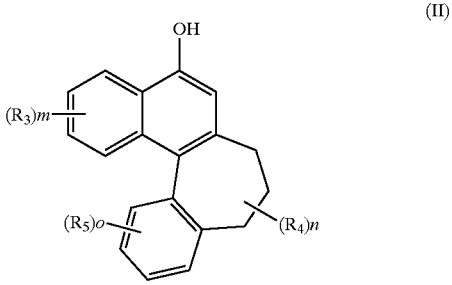

in which $R_3$, $R_4$, $R_5$, m, n, and o are as defined as in claim 1.

6. A (co)polymer and/or reticulate obtained by polymerising and/or cross-linking at least one monomer comprising a compound according to claim 1.

7. A photochromic material, wherein said photochromic material is constituted by:

a compound according to claim 1, a mixture at least two compounds according to claim 1, or a mixture of at least one compound according to claim 1 with at least one other photochromic compound of another type and/or at least one non-photochromic colouring agent.

8. A photochromic composition comprising:

at least one compound according to claim 1, and/or at least one linear or cross-linked (co)polymer which contains, in its structure, at least one compound according to claim 1, and optionally, at least one other photochromic compound of another type and/or at least one non-photochromic colouring agent and/or at least one stabilising agent.

9. A (co)polymer matrix comprising at least one compound according to claim 1.

10. A (co)polymer matrix comprising at least one composition according to claim 8.

11. A (co)polymer matrix comprising at least one co(polymer) and/or reticulate according to claim 6.

12. A (co)polymer matrix according to claim 9 further comprising one or more (co)polymers selected from the group consisting of:
- those obtained from alkyl, cycloalkyl, (poly or oligo) ethylene glycol or aryl or arylalkyl mono-, di-, tri-, or tetraacrylate or mono-, di-, tri-, or tetramethacrylate which is optionally halogenated or which optionally comprises at least one ether and/or ester and/or carbonate and/or carbamate and/or thiocarbamate and/or urea and/or amide group;
- polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral;
- those obtained from difunctional monomers having the formula below:

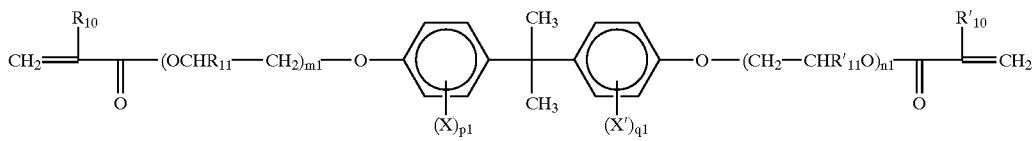

in which:
$R_{10}$, $R'_{10}$, $R_{11}$, and $R'_{11}$ are identical or different and represent, independently, a hydrogen or a methyl group;
$m_1$ and $n_1$ are, independently, integers between 0 and 4, inclusive;
X and X', which are identical or different, are a halogen;
$p_1$ and $q_1$ are, independently, integers between 0 and 4, inclusive; and
copolymers of at least two types of copolymerisable monomers selected from the precursor monomers of the polymers listed above.

13. An ophthalmic or solar article comprising at least one compound according to claim 1.

14. An ophthalmic or solar article according to claim 13 comprising a lens, a glazing, an optical device, or a combination thereof.

15. An ophthalmic or solar article comprising at least one composition according to claim 8.

16. An ophthalmic or solar article according to claim 15 comprising a lens, a glazing, an optical device, or a combination thereof.

17. An ophthalmic or solar article comprising at least one (co)polymer and/or reticulate according to claim 6.

18. An ophthalmic or solar article according to claim 17 comprising a lens, a glazing, an optical device, or a combination thereof.

19. An ophthalmic or solar article comprising at least one (co)polymer matrix according to claim 9.

20. An ophthalmic or solar article according to claim 19 comprising a lens, a glazing, an optical device, or a combination thereof.

* * * * *